United States Patent [19]

Heinz et al.

[11] 4,140,129
[45] Feb. 20, 1979

[54] BEAM DEFINING SYSTEM IN AN ELECTRON ACCELERATOR

[75] Inventors: Lothar Heinz; Leonhard Taumann, both of Lafayette, Calif.

[73] Assignee: Applied Radiation Corporation, Walnut Creek, Calif.

[21] Appl. No.: 787,310

[22] Filed: Apr. 13, 1977

[51] Int. Cl.² .............................................. A61N 1/00
[52] U.S. Cl. ................... 128/404; 250/503; 250/513
[58] Field of Search ............... 128/404, 405, 413, 422, 128/362, 395, 396, 399; 250/511–513, 503

[56] References Cited

U.S. PATENT DOCUMENTS

| 2,388,830 | 11/1945 | Cotton | 128/404 X |
| 3,114,043 | 12/1963 | Thomas et al. | 250/511 X |
| 3,764,808 | 10/1973 | Lackey et al. | 250/511 X |
| 3,969,629 | 7/1976 | McIntyre | 250/503 |

FOREIGN PATENT DOCUMENTS 345409 1/1937 Italy ......................... 250/513
913008 12/1962 United Kingdom ............... 128/404

OTHER PUBLICATIONS

Fischer X-Ray . . . Accessories, Catalog No. 14, May 1924, pp. 45–47, Fischer & Co., Inc.

*Primary Examiner*—Lee S. Cohen
*Attorney, Agent, or Firm*—Hill, Gross, Simpson, Van Santen, Steadman, Chiara & Simpson

[57] ABSTRACT

A beam defining system for an electron accelerator has an adjustable collimator with an accessory holder attached thereto for retaining an electron applicator. The electron applicator has an applicator wall which encloses an electron beam cone from the collimator. A frame-shaped spacer which can be brought into contact with the patient is attached to the applicator wall. A frame-shaped limiting aperture additional to limiting members in the collimator are provided on the applicator wall in order to limit the electron-beam cone at marginal regions facing away from the beam defining system.

14 Claims, 4 Drawing Figures

BEAM DEFINING SYSTEM IN AN ELECTRON ACCELERATOR

BACKGROUND OF THE INVENTION

1. Field of the Invention

The invention relates to a beam defining system for an electron accelerator. The beam defining system has an adjustable collimator and an accessory holder for the attachment of, among other items, an electron applicator formed of an applicator wall enclosing an electron-beam cone and a frame-shaped spacer which is attached at the applicator wall and which can be brought into contact with the patient.

2. Description of the Prior Art

When patients are subjected to electron beams due to the scattering of electrons in air, it is necessary to limit the electron-beam cone by an enclosed path bridging the gap between the beam defining system and the patient. It is known in the art to attach electron applicators to an accessory holder of the beam defining system. These electron applicators are placed into direct contact with the patient. They have the further function of fixing the distance of the patient from the beam defining system, a distance which must be precisely maintained for dosage computations. A few electron applicators of this type were previously made transparent to simplify positioning. One of the disadvantages of prior art devices was the lack of direct accessibility to the exposed field such as the skin surface of the patient with markings applied thereto. This disadvantage has been eliminated in such a way that electron applicators have been shortened 10 to 20 cm and a frame-shaped spacer is mounted to the electron applicator by supports in order to set the desired spacing. In the case of such an electron applicator, however, there is the disadvantage that the beam quality in the marginal regions of the beam cone is effected by increased low energy portions of the beam. Due to the energy-dependent range of the electrons, a high dosage decrease in the marginal regions of the beam cone is present deep within the patient's tissue as compared to the center regions of the beam cone. It is also considered a disadvantage that even minor deviations of the symmetry axis of the applicator from the center beam, i.e., the axis of the beam cone, causes clearly changed dosages in the marginal regions of the beam cone.

SUMMARY OF THE INVENTION

It is an object of the present invention to develop an applicator for electron radiation which permits not only evenly distributed high dosage radiation in the entire beam cone, but also equal radiation quality, i.e., electron spectra of the same energy. In addition, this applicator should be less critical as to centering with respect to the beam cone.

In the case of a beam defining system of this invention, a wall of the applicator has an additional frame-shaped limiting aperture in order to limit the electron-beam cone at its edges which are facing away from the beam defining system. Due to the additional frame-shaped limiting aperture in the electron applicator, it results that all scattered or secondary electrons, respectively, which had been previously produced in the marginal region of the beam cone, are blocked out. Thus, the dosage decreases only slightly in the marginal regions of the beam cone (maximum 25%). In the case of the prior art, electron applicators without a rectangular shaped aperture in the electron applicators had dosages in the marginal regions which were balanced by the scattered electrons produced at the applicator walls. This scattered electron portion, however, did not contribute to a higher dosage performance deep within the object to be subjected to radiation. They only increase the surface dosage, and thus the skin exposure of the patient. Due to the frame-shaped limiting aperture and the reduced scattered beam portion, it is also possible to make centering of the electron applicator with respect to the beam cone less critical. An important increase of operational safety is obtained when the electron applicator is equipped with a carrier frame which is standardized, has outer dimensions which correspond to the accessory holder of the beam defining system, and which has a sensible coding corresponding to the applicator width. Thus, a technique is provided for controlling or monitoring the electron accelerator.

In a further development of the invention, faulty adjustments are avoided if the accessory holder of the beam defining system is provided with sensors for detecting the coding on the carrier frame. These sensors are connected to switching means for a monitoring circuit and a follow-up control for the collimator. Thus, false aperture limiting of the collimator may be avoided when the electron applicator is inserted. It is also possible to indicate the type of electron applicator which is inserted to the operator at the control desk.

In another development of the invention the homogeneity of the limited electron beam can be even further improved when the applicator wall, except for the additional frame-shaped limiting aperture, has sufficient width so as to be beyond the limited beam cone, a result stemming from coding of the applicator. This results in less scattering radiation being produced in the electron applicator. It is essentially only produced at the collimators and at the additional frame-shaped limiting aperture of the electron applicator. In this manner, a further spectrum improvement of the beam quality and, finally, a lesser skin dosage will result.

In a further development of the invention, the adjustment to a patient who is to be submitted to radiation is facilitated when the spacer is mounted in the beam direction such that with an elastic force it is biased away from the beam defining system and is retained by at least one stop at a desired spacing. In the case of this embodiment of the spacer, the patient can move in the event of emergency and an injury to the patient doesn't result if a faulty operation of the setting drives of the table and/or beam defining system occurs.

Supervision of appropriate use of the spacer at the patient is facilitated when the spacer is mounted with supports having marks which indicates shift from contact at the stop. Thus, the operator may observe by viewing the markings whether the spacer is resting lightly against the patient.

Greater supervision results when the spacer is coupled with switch means which can be actuated by way of contact with the stops. This will produce an electric signal which may be supplied to either an indicator device at the control desk or which may cause the immediate interruption of the radiation exposure when the spacer is pressed back by the patient.

DESCRIPTION OF THE PREFERRED EMBODIMENTS

Figure 1:
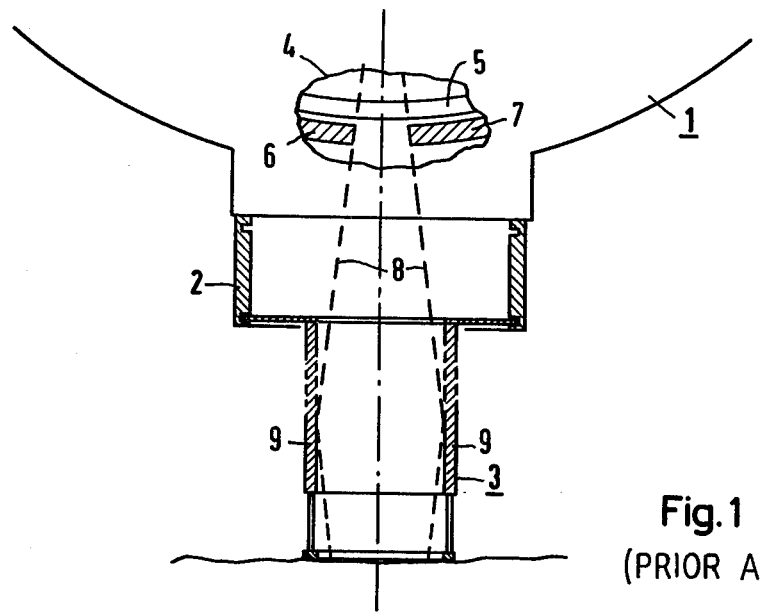
FIG. 1 illustrates a partial section of a beam defining system of an electron accelerator with a prior art electron applicator.

An electron applicator 3 of the prior art is schematically shown in FIG. 1 which illustrates a beam defining system 1 of the electron accelerator having an accessory holder 2 attached at the beam defining system. A prior art electron applicator 3 is placed into the accessory holder 2. The X-ray aperture plates 5, 6, 7 of the collimator seen through the partial cutaway 4 are completely opened during operation for the purpose of producing an electron beam cone instead of an X-ray cone so that the electron beam cone 8 will slightly touch the tube wall 9 of the electron applicator 3. Thus, additional secondary electrons are produced in the marginal region of the tube wall which are scattered into the beam cone. This compensates the typical dosage performance drop-off in the marginal region of the beam cone. In order to be better able to approach the marks for the radiation field applied on the skin surface of the patient and also to be better able to adapt the electron applicator to the radiation field, the electron applicator has been shortened 10 to 15 cm and the remaining distance is occupied by a frame-shaped spacer which is firmly attached to the tube wall 9 of the electron applicator.

Figure 2:
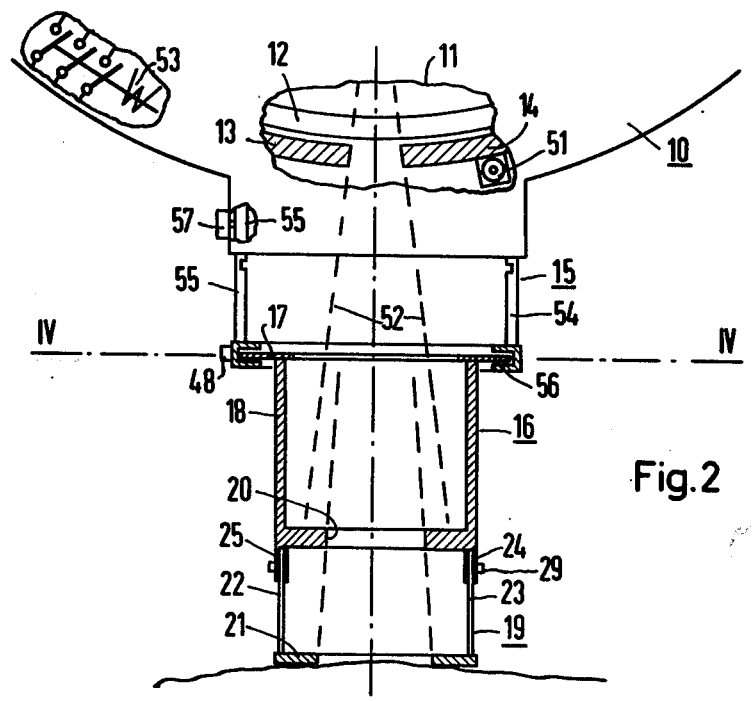
FIG. 2 illustrates a partial section of a beam defining system of an electron accelerator with an attached electron applicator of this invention.
Figure 3:
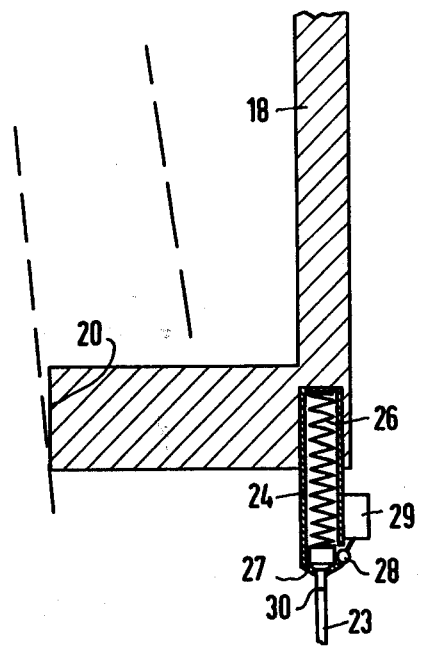
FIG. 3 is an enlarged view illustrating attachment of supports of a spacer of this invention.

FIG. 2 shows a partial section of a beam defining system 10 of an electron accelerator. The adjustable X-ray aperture plates 12, 13, 14 of the collimator are shown at the partial cutaway 11. An accessory holder 15 has been attached to the beam defining system 10. An electron applicator 16 which slides into the accessory holder is also shown. The electron applicator 16 consists of a rectangular carrier frame or plate 17 having outer dimensions corresponding to the dimensions of the accessory holder 15. A tube wall 18 is attached to the carrier frame and surrounds the beam cone. A spacer 19 is provided at a given distance from the tube wall 18. As can be easily recognized from FIG. 2, the tube wall 18 is provided with an additional frame-shaped limiting aperture 20 at its end which is turned away from the beam defining system 10. This additional frame-shaped limiting aperture serves for additional field formation. The spacer 19 consists of a plastic frame 21 (preferably made of polystyrol) which is mounted via four supports 22, 23 at a given spacing in front of the patient-facing frontal surface of the tube wall 18. The supports 22, 23 shown in the enlarged representation of FIG. 3, are slidably mounted in casings 24, 25 attached at the tube wall parallel to a symmetry axis of the electron applicator. The supports each have enlarged portions at their ends which are slidably received in the casings 24, 25. They are biased by a spring 26 against a stop 27. At the position where the enlarged portions of the supports 22, 23 are supported at the stop 27, a spring-loaded sensor 28 is provided for contact with the support at the stop 27. The sensor 28 serves for actuating an electric switch 29. The position of each support is characterized by a colored ring 30 which is exposed outside the casings 24, 25 during contact with the stop 27.

Figure 4:
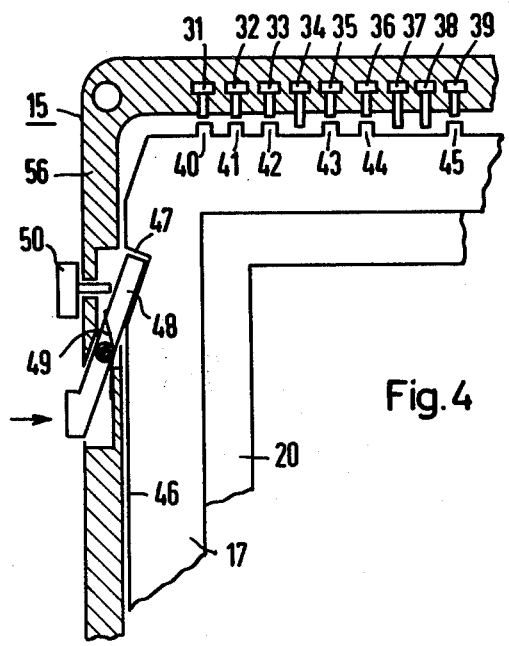
FIG. 4 is a sectional view through the accessory holder along with a selected carrier frame inserted.

In the sectional view along the insertion plane of the accessory holder 15 shown in FIG. 4, the arrangement of the switches 31 through 39 is shown. These switches sense the cams 40 through 45 provided on the carrier frame 17. The cams are arranged on the carrier frame in accordance with a code which is representative of the width of the electron applicator 16. At one of the lateral guides 46 of the carrier frame 17 a recess 47 has been provided for a latch 48. This latch, which is loaded by a spring 49, secures the electron applicator in its fully inserted position. The position of the latch is sensed by a further switch 50. This switch 50 is connected in series with other switches which sense the cams 40 through 45 on the carrier frame of the electron applicator 16.

When the electron applicator 16 is slid into the accessory holder 15 of the beam defining system 10, the applicator must be pushed in up to the stop until the latch 48 locks so that the switch 50 arranged at the latch and sensing its position is actuated so as to permit the release of radiation. In this position, the electron applicator 16 is locked in the accessory holder 15. Also, the cams 40 through 45 at the insertion end of the carrier frame 17 are also pressed against the switches 31 through 39 positioned in alignment with the insertion end of the frame. These switches thus determine the coding of the cams. In a manner which is not shown here, they are connected with the setting drive 51 for the collimator aperture plates 12, 13, 14 of the beam defining system 10 and readjust the collimator in accordance with the sensed coding, and thus in accordance with the clear width of the electron beam applicator 16. It would also be possible to adjust the aperture plates by hand and to unlock the radiation system in the case of a coincidence of the aperture plate adjustment with the coding of the applicator sensed by the switches. The limiting adjustment of the electron beam 52 results from the above when the electron applicator is inserted such that the electron beam does meet the frame-shaped aperture 20 of the tube wall of the electron applicator but does not touch the tube wall 18 itself. Thus production of secondary electrons at the tube wall is avoided. The secondary electrons produced at the X-ray aperture plates of the collimator 12, 13, 14 are blocked out to a great extent by the additional frame-shaped limiting aperture 20.

The spacer 19, which, in its rest position is held by the springs 26 at a given spacing from the frame-shaped limiting aperture 20 and thus from the beam defining system 10, must be brought into contact with the patient during radiation exposure. Thus, the previously determined radiation spacing is maintained. At this spacing, the polystyrol frame 21 of the spacer 19 performs as an additional beam limiting aperture additional to the frame-shaped limiting aperture 20 of the electron applicator 16 and compensates widening of the electron beam 52 caused by air molecule scattering. Due to the slidable nature of the spacer 19 perpendicular to the beam direction, it neither will hinder a possible movement of the patient during the set-up procedure nor the accessability to markings for the radiation field placed on the skin surface of the patient. In addition, it prevents injuries to the patient in case of faulty operation of the setting drives. The correct positioning of the patient at the spacer 19 can visually be controlled in such a way that it is determined whether colored rings 30 protrude from the guide bushings 24, 25 or not. If the colored rings cannot be recognized, the spacer 19 is pressed in too far. The additional switches 29 at the bushing 24 control the position of the supports 22, 23 of the spacer 19. Due to the switches 29, which are mutually series-connected, the fully extended position of the spacer 19 is monitored and indicated at the control desk. Possibly they may be connected in series to a further relay 53 blocking the radiation system. It is also possible to mount the slide-in frame 56 of the accessory holder 15 in such a way that it can be slid into the radiation head 10 via columns 54, 55 in order to obtain free mobility around the patient during the exposure to X-rays. The position of the accessory holder is controlled via a switch 57. This switch is connected too in series to the relay 53 blocking the radiation system.

Although various minor modifications may be suggested by those versed in the art, it should be understood that it is intended to embody within the scope of the patent warranted hereon, all such embodiments as reasonably and properly come within the scope of this contribution to the art.

We claim:

1. A beam defining system for an electron accelerator which produces an electron beam cone, comprising:
   (a) an adjustable collimator for producing the beam cone;
   (b) an accessory holder attached adjacent the collimator;
   (c) an electron applicator releasably attached to the accessory holder, said applicator including a tube wall positioned so as to enclose the electron beam cone from the collimator and a frame-shaped spacer movably attached to the tube wall and movable independently of the tube wall into contact with a patient to be treated, said tube wall having a first frame-shaped limiting aperture means associated with the tube wall for limiting edges of the electron beam cone facing away from the beam defining system; and
   (d) said frame-shaped spacer having a frame defining a second limiting aperture means having a periphery larger than a periphery of the first frame-shaped limiting aperture means, the second aperture means limiting the same edges of the electron beam cone as the first aperture means when the second aperture means is substantially at a predetermined distance from the collimator and in contact with the patient.

2. A beam defining system in accordance with claim 1, characterized in that said electron applicator has attached thereto a standardized carrier frame which has outer dimensions which correspond to dimensions of the accessory holder of the beam defining system and which is provided with a sensible coding related to a width of the applicator tube wall.

3. A beam defining system in accordance with claim 2, characterized in that the carrier frame has a groove therein and the accessory holder of the beam defining system is provided with a latch engaged with the groove of the carrier frame when the frame is fully inserted in the accessory holder.

4. The beam defining system of claim 2 in which sensor means is provided for sensing the sensible coding and for initiating an adjustment of the collimator in relation to the sensible coding which is sensed.

5. A beam defining system in accordance with claim 2, characterized in that the tube wall includes means corresponding to the coding which prevents the tube wall from intersecting the beam cone except for the frame-shaped limiting aperture means, said means comprising a width of the tube wall.

6. A beam defining system for an electron accelerator which produces an electron beam cone, comprising:
   (a) an adjustable collimator for producing the beam cone;
   (b) an accessory holder attached adjacent the collimator;
   (c) an electron applicator releasably attached to the accessory holder, said applicator including a tube wall positioned so as to enclose the electron beam cone from the collimator and a frame-shaped spacer attached to the tube wall and movable into contact with a patient to be treated, said tube wall having a frame-shaped limiting aperture means associated with the tube wall for limiting edges of the electron beam cone facing away from the beam defining system; and
   (d) the accessory holder of the beam defining system being equipped with sensor means for detecting a coding on the electron applicator and switch means for a monitoring circuit and follow-up control for the adjustable collimator being connected to said sensor means.

7. A beam defining system for an electron accelerator which produces an electron beam cone, comprising:
   an adustable collimator for producing the beam cone;
   (b) an accessory holder attached adjacent the collimator;
   (c) an electron applicator releasably attached to the accessory holder, said applicator including a tube wall positioned so as to enclose the electron beam cone from the collimator and a frame-shaped spacer attached to the tube wall and movable into contact with a patient to be treated, said tube wall having a frame-shaped limiting aperture means associated with the tube wall for limiting edges of the electron beam cone facing away from the beam defining system; and
   (d) said frame-shaped spacer having mounting means for shifting the spacer along a direction of the beam, said mounting means including a stop means and an elastic means biasing the spacer away from the beam defining system against the stop means, said stop means defining a desired spacing of the beam defining system with respect to the patient.

8. A beam defining system in accordance with claim 7, characterized in that the spacer is mounted with supports which are provided with marking means for revealing shifts of the spacer from contact against the stop means.

9. A beam defining system in accordance with claim 7, characterized in that a switch means for connection to a monitoring circuit for the electron accelerator is associated with the spacer, said switch means being actuated when said spacer is biased against the stop means.

10. A beam defining system for an electron accelerator which produces an electron beam cone, comprising:
   (a) an adjustable collimator for producing the beam cone;
   (b) an accessory holder attached adjacent the collimator;
   (c) an electron applicator releasably attached to the accessory holder, said applicator including a tube wall positioned so as to enclose the electron beam cone from the collimator and a frame-shaped spacer attached to the tube wall and movable into contact with a patient to be treated, said tube wall having a frame-shaped limiting aperture means associated with the tube wall for limiting edges of the electron beam cone facing away from the beam defining system;

(d) said electron applicator having attached thereto a standardized carrier frame having a groove therein and which has outer dimensions which correspond to dimensions of the accessory holder of the beam defining system and which is provided with a sensible coding related to a width of the applicator tube wall;

(e) the accessory holder of the beam defining system being provided with a latch engaged with the groove of the carrier frame when the frame is fully inserted in the accessory holder; and (f) a switch means being associated with the latch for sensing its position and which also permits switching off the electron accelerator.

11. A beam defining system in accordance with claim 10, characterized in that the switch means which senses the position of the latch is connected in series with a further switch means of the accessory holder for sensing the sensible coding to control the adjustable collimator.

12. A beam defining system for an electron accelerator which produces an electron beam cone, comprising:
(a) an adjustable collimator for producing the beam cone;
(b) an accessory holder attached adjacent the collimator;
(c) an electron applicator releasably attached to the accessory holder, said applicator including a tube wall positioned so as to enclose the electron beam cone from the collimator and a frame-shaped spacer attached to the tube wall and movable into contact with a patient to be treated, said tube wall having a frame-shaped limiting aperture means associated with the tube wall for limiting edges of the electron beam cone facing away from the beam defining system; and
(d) the electron applicator including a carrier plate and the accessory holder includes a slide-in frame receiving the carrier plate, said accessory holder also including column means attached to the slide-in frame for shifting the accessory holder into a desired position in the beam defining system from an alternate position for permitting free mobility of the system while the patient is exposed to X-rays.

13. A beam defining system in accordance with claim 12, characterized in that switch means are provided for monitoring a desired position of the accessory holder.

14. A beam defining system for an electron accelerator which produces an electron beam cone, comprising:
(a) a collimator having adjustable limiting aperture plates for producing the beam cone;
(b) an accessory holder attached adjacent the collimator;
(c) an electron applicator detachably connected to the accessory holder, said electron applicator including a surrounding wall portion positioned so as to enclose the electron beam cone from the collimator, and a surrounding spacer portion positioned so as to further enclose the beam cone;
(d) coding means on the electron applicator for encoding a width dimension of the applicator; and
(e) sensing means on the accessory holder for sensing said coding means and monitoring the applicator width dimension relative to electron beam width.

* * * * *